United States Patent
Jones

(10) Patent No.: US 11,077,149 B1
(45) Date of Patent: *Aug. 3, 2021

(54) METHOD FOR THE COLLECTION AND USE OF AMNIOTIC FLUID

(71) Applicant: PENSARA, INC, Richmond, TX (US)

(72) Inventor: Geoffrey Charles Jones, Missouri City, TX (US)

( * ) Notice: Subject to any disclaimer, the term of this patent is extended or adjusted under 35 U.S.C. 154(b) by 497 days.

This patent is subject to a terminal disclaimer.

(21) Appl. No.: 16/042,462

(22) Filed: Jul. 23, 2018

Related U.S. Application Data

(63) Continuation-in-part of application No. 15/614,550, filed on Jun. 5, 2017, now abandoned, and a continuation-in-part of application No. 14/638,574, filed on Mar. 4, 2015, now Pat. No. 10,029,035.

(60) Provisional application No. 62/353,964, filed on Jun. 23, 2016.

(51) Int. Cl.
*A61M 1/00* (2006.01)
*A61M 5/178* (2006.01)
*A61K 35/50* (2015.01)

(52) U.S. Cl.
CPC .............. *A61K 35/50* (2013.01); *A61M 1/008* (2013.01); *A61M 1/0094* (2014.02); *A61M 1/0096* (2014.02); *A61M 5/178* (2013.01); *A61M 2202/0468* (2013.01); *A61M 2202/0494* (2013.01)

(58) Field of Classification Search
CPC . A61K 35/50; A61M 1/0096; A61M 1/00808; A61M 1/00; A61M 2202/0494; A61M 2202/0468
See application file for complete search history.

(56) References Cited

U.S. PATENT DOCUMENTS

| | | | | |
|---|---|---|---|---|
| 4,957,629 A | * | 9/1990 | Smith | B01D 29/01 128/205.12 |
| 2008/0299087 A1 | * | 12/2008 | Tseng | A61K 9/0014 424/93.7 |
| 2011/0066182 A1 | * | 3/2011 | Falus | A61L 24/043 606/214 |
| 2014/0336600 A1 | * | 11/2014 | Harrell | A61B 10/0048 604/319 |
| 2016/0256500 A1 | * | 9/2016 | White | A61K 35/50 |

* cited by examiner

*Primary Examiner* — Ariana Zimbouski
*Assistant Examiner* — Gabriella E Burnette

(57) ABSTRACT

Disclosed is a method for the collection, processing and reuse of amniotic fluid at a C-section site. The method is conducted coincident with and in the operating room wherein the caesarian section is performed. In the method, amniotic fluid is suctioned from the caesarian section collection site using a vacuum line system which includes a canister positioned along the vacuum line. The canister has a port whereby the amniotic fluid can be removed from the canister. The amniotic fluid can be then be mixed with a coagulant or sealant and applied to the wound site of the cesarean section patient. Placental aspirate may also be collected, processed and used in accordance with the method of the present invention.

6 Claims, 5 Drawing Sheets

METHOD FOR THE COLLECTION AND USE OF AMNIOTIC FLUID

CROSS-REFERENCE TO RELATED APPLICATIONS

The present application is a continuation-in-part of U.S. application Ser. No. 14/638,574, filed on Mar. 4, 2015, presently pending. The present application is also a continuation-in-part of U.S. application Ser. No. 15/614,550, filed on Jun. 5, 2017, presently pending.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to the field of the collection of amniotic fluid and placental aspirate. More particularly, the present invention relates to a method wherein amniotic fluid and placental aspirate can be collected at the cesarean section site, processed if necessary, and reused as a medication for the patient.

2. Description of Related Art Including Information Disclosed Under 37 CFR 1.97 and 37 CFR 1.98

Caesarean section, or C-section, is the delivery of a baby through a cut in the mother's lower abdomen and the uterus. Today, it is one of the most frequently performed surgeries in the world, more commonly performed than gallbladder removal, hysterectomy, or tonsillectomy. A C-section may be lifesaving for the baby or the mother or both.

In a C-section, the first incision made is either a vertical incision in the middle of the abdomen, from below the navel down to the pubic bone, or a transverse or "bikini cut" incision, called an annesteil incision, from side to side just above the pubic hairline. The bikini cut incision is more common, because it heals better, has a shorter recovery time, and is more cosmetically acceptable. After going through the various layers of the abdominal wall and opening the bladder fold of peritoneum, the lower segment of the uterus is exposed. An incision is then made in the uterine wall. Usually, the incision is horizontal; this is preferred as it heals better and bleeds less. However, under some circumstances, it is necessary for the doctor to make a vertical incision in the uterus.

Recovery from a C-section generally takes longer than a vaginal delivery. During a C-section, the amniotic fluid and placenta are typically suctioned away or otherwise disposed of. This presents a missed opportunity, as amniotic fluid is known to have certain beneficial components, including growth factors. Placental aspirate also known to have beneficial components, including stem cells and platelets. The stem cells found in the placental aspirate could potentially be very useful, as the stem cells are less limited in their application than those of the most commonly available source of stem cells, bone marrow.

Typically, operating rooms are provided with a series of vacuum components, including a plurality of the vacuum suction lines whereby the liquid such as amniotic fluid can be removed from the surgical site and disposed of or used at a later time.

The separation of the components of liquid, most commonly blood, but is well-known. Numerous patents have issued in the past relating to separation of the components of blood, typically at utilizing centrifuges. U.S. Pat. No. 5,242,606 (the '606 patent) issued on Sep. 7, 1993 to Braynin et al. The '606 patent is an example of such a device for separating the plasma from whole blood. In the '606 patent, an analytical rotor is used having a sample application port in the upper surface thereof. Blood is introduced into the sample application port and metered into a metered chamber by capillary flow while the rotor remain stationary. Excess blood passes into an overflow chamber by capillary flow, either simultaneously with the metered flow or after opening of a vent in the overflow chamber. Subsequent rotation of the rotor causes metered blood in the metering chamber to flow into receiving chamber, typically a plasma separation chamber.

Cyclonic separation is also well known. For example, U.S. Patent Publication No. 2014/0047986, published on Feb. 20, 2014 to Robinson, describes systems and methods for salvaging red blood cells from patients during a surgical procedure. A system is described for cyclonically extracting blood from blood-soaked absorbent surgical materials such as surgical sponges, gauze, tape, and the like. The collected blood and fluids from these materials can be transferred to a cell salvage machine for harvesting viable red blood cells for autotransfusion.

Filtration of obstetrical fluids is also known, as well as filtration along a suction line. For example, refer to U.S. Pat. No. 4,957,629 (the '629 patent), issued on Sep. 18, 1992 Smith et al. The '629 patent describes a filter for obstetrical fluids and particulate matter having an enclosure containing a first chamber and a second chamber. The first chamber has a solid partition forming first and second cavities in the first chamber. The first cavity has an inlet and the second cavity has an outlet. The second chamber contains a filter and the edge of the partition is pressed against the surface of the filter.

The collection and reuse of amniotic fluid is also contemplated by others in the field. For example, refer to U.S. Patent Publication No. 2014/0336600 (the '600 publication), published on Nov. 13, 2014 to Harrell. The '600 publication describes a method for obtaining sterile amniotic fluid, as well as uses for such fluid. The '600 publication describes the use of a suction or a pump for collecting the amniotic fluid, as well as separation of cells such as growth factors and stem cells from the amniotic fluid. The '600 publication describes the separation of the growth factors and stem cells in a centrifuges remote from the collection site. Further, the '600 publication does not contemplate the autologous use of the amniotic fluid on the patient.

As such, a need developed for a system and method wherein amniotic fluid and placental aspirate, including stem cells and other beneficial cells therein, could be reused on the same patient so as to assist in the healing of the C-section wound.

U.S. application Ser. No. 14/638,574, filed on Mar. 4, 2015 by the present applicant, will issue as U.S. Pat. No. 10,029,035 on Jul. 23, 2018 (the '035 patent). The '035 patent claims a method wherein amniotic fluid and placental aspirate are collected, processed using a specialized canister described hereinbelow, and reused on the patient. The processing of the amniotic fluid and placental aspirate was undertaken in order to separate cells such as growth factors and stems cells (i.e. heavier cellular material) so as to enhance the efficacy of the fluid as a medication.

In practice, it was unexpectedly found that un-processed collected amniotic fluid provides healing properties similar to those of the processed fluid, without the additional time and cost associated with processing of the fluid using the specialized container. As such, the applicant has developed the method of autologous use of amniotic fluid as described below.

It is an object of the present invention is to provide such a system and method to accomplish this goal.

It is another object of the present invention to provide a method for the collection of amniotic fluid which can be used with existing operating room equipment.

It is another object of the present invention to provide a method for the collection and processing of amniotic fluid and placental aspirate which allows for instant reuse of the beneficial components of the amniotic fluid and placental aspirate.

It is another object of the present invention to provide a method for the collection and processing amniotic fluid and placental aspirate which is easy to use and does not require substantial amount of time in addition to the standard procedure.

It is another object of the present invention to provide a method for the collection and use of amniotic fluid and placental aspirate which utilizes the amniotic fluid and placental aspirate to speed healing of a cesarean section wound.

These and other objects and advantages of the present invention will become apparent from a reading of the attached specification and appended claims.

BRIEF SUMMARY OF THE INVENTION

The present invention is a method for collection and use of amniotic fluid including the following steps: (1) coincident with a caesarian section procedure, suctioning amniotic fluid from a caesarian section collection site using a vacuum line; (2) passing the suctioned amniotic fluid into a canister positioned along or in communication with the vacuum line; (3) removing at least some of the passed amniotic fluid from the canister; (4) mixing the removed amniotic fluid with either of a coagulant or a sealant; and (5) applying the mixed amniotic fluid to the caesarian section collection site using an applicator, wherein each of the steps are conducted in a single operating room.

In the present invention, the step of removing may include: (1) providing a port on the canister; (2) inserting a syringe needle into the port; and (3) drawing amniotic fluid into an interior of the syringe needle. The coagulant or sealant may be calcium chloride.

The method may also include the following steps: (1) collecting placental aspirate; (2) passing the collected placental aspirate into a canister; (3) removing at least some of the passed placental aspirate from the canister; (4) mixing the removed placental aspirate with either of a coagulant or a sealant; and (5) injecting the mixed placental aspirate into the caesarian section collection site.

In the present invention, the at least some of the passed amniotic fluid may be heavier cellular material. In this case, the method includes the additional step of separating heavier cellular material from the passed amniotic fluid inside the canister.

This foregoing Section is intended to describe, with particularity, the preferred embodiment of the present invention. It is understood that modifications to these preferred embodiments can be made within the scope of the present claims. As such, this Section should not to be construed, in any way, as limiting of the broad scope of the present invention. The present invention should only be limited by the following claims and their legal equivalents.

BRIEF DESCRIPTION OF THE SEVERAL VIEWS OF THE DRAWINGS

FIG. 1 is a schematic view showing a canister for use in the preferred embodiment of the method of the present invention.

DETAILED DESCRIPTION OF THE INVENTION

Figure 1:
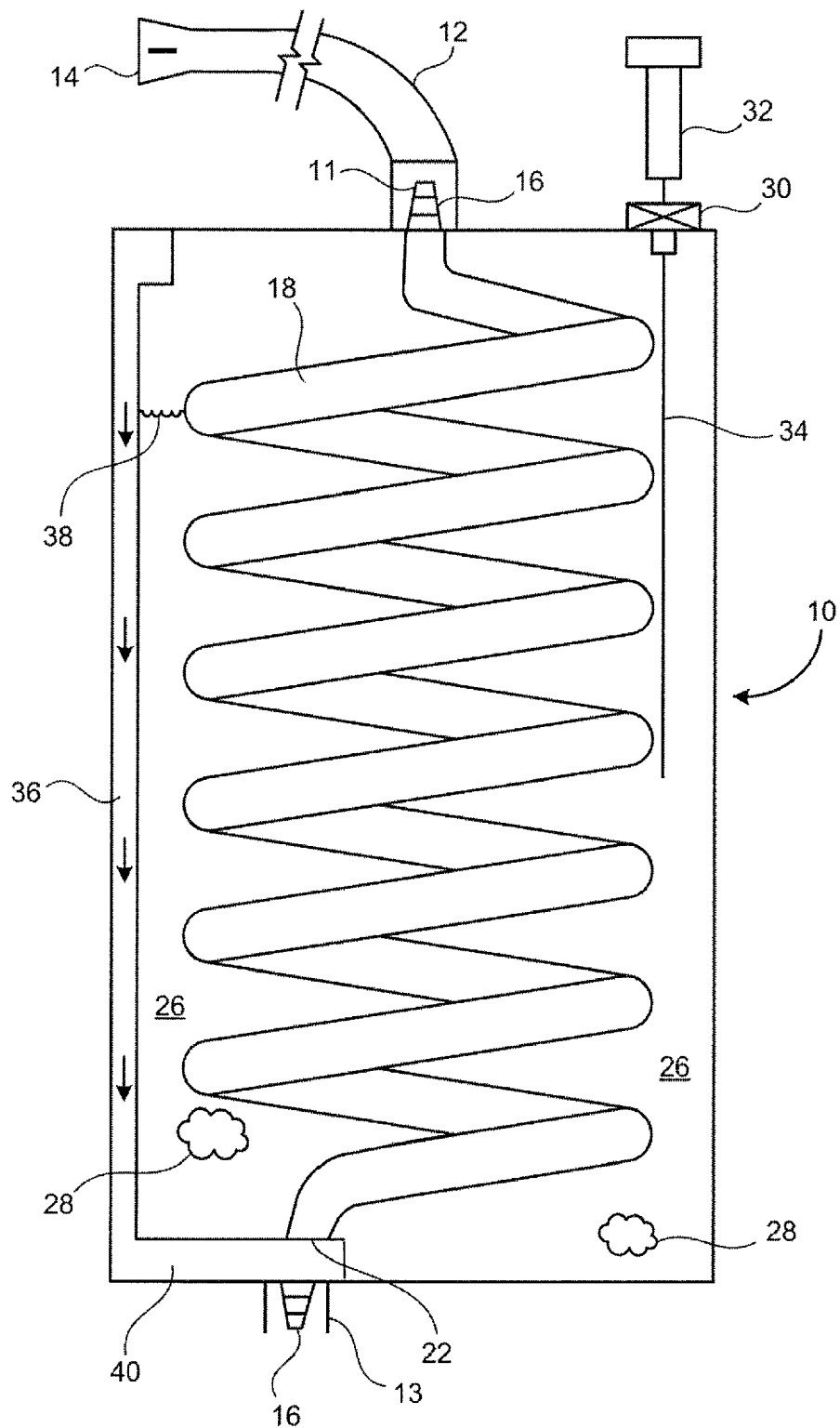
FIG. 1 is a schematic view showing a canister for use in a method of the present invention.

Referring to FIG. 1, there is shown a sectional, schematic view of the canister 10 of the system of the present invention as originally disclosed in U.S. application Ser. No. 14/638, 574. The canister 10 is positioned along a vacuum line 12. The vacuum line 12 has a suction tip 14 at an end thereof. The vacuum line 12 is connected at connection 16 to the inlet 11 and outlet 13 of the canister 10 of the present invention. As will be described hereinafter below, amniotic fluid is collected using the suction tip 14 and introduced into the canister 10, wherein heavier cellular material is collected and the remaining amniotic fluid exits through a connection 16 adjacent the outlet 13 of the canister 10 and is disposed of or processed further. The inlet 11 and outlet 13 of the canister generally comprise the connections 16 and are in fluid communication with the interior of the canister 10.

As will be described hereinbelow, the canister 10 of the present invention may also be used to process placental blood, or placental aspirate, collected from the caesarian section site.

The canister 10 of the present invention may include a coil 18. The coil 18 defines a pathway whereby the amniotic fluid or placental aspirate is urged into a cyclonic motion. A chamber 26 is defined by the interior of the canister 10 and the exterior of the coil 18. As such, preferably, the chamber 26 surrounds the coil 18.

The coil 18 is may be a hollow tubular coil. The coil 18 extends in a spiral shape from the inlet of the canister towards the outlet. Adjacent the outlet 13 of the canister, the coil 18 has a slotted opening 22. As shown hereinbelow, the slotted opening 22 opens to both the outlet 13 of the canister 10 and to the chamber 26. The shape of the coil 18 urges heavier cellular material towards the outside of the coil, and thus, the heavier cellular material exits the slotted opening 22 on the side and enters the chamber 26.

This heavier cellular material 28 collects at a bottom of the chamber 26. Liquid can also accumulate within the chamber 26 as indicated by the liquid accumulation level 38 shown on the left side of the chamber 26. The remaining fluid exits the chamber 26 through the outlet 13 of the canister 10 and back into the vacuum line 12.

The canister 10 is provided with a port 30. The port 30 is preferably suitable for the receipt of a needle 34 of a syringe 32 (preferably 10 cc). The port 30 allows for access of the chamber 26, which functions as a cellular accumulation chamber. As shown in FIG. 1, the needle 34 can extend down into the chamber 26 so as to reach the accumulated cellular materials 28. The syringe 32 can then be used so as to remove the cellular materials 28 from the chamber 26. Preferably, the port 30 is provided adjacent to the inlet 11 of the canister 10. However, various other locations and ways of evacuating the accumulated cellular material 28 are possible within the concept of the present invention.

The canister 10 is generally cylindrical, and can be tilted such that the cellular materials 28 shown on the left side of the canister 10 in FIG. 1 can be allowed to move towards a location wherein the needle 34 of the syringe 32 can access the cellular material 28.

In one embodiment of the present invention shown in FIG. 1, a second vacuum line 36 is provided. The second vacuum line 36 generally runs from an upper end of the canister 10, in communication with the chamber 26, and down to the outlet 13 of the canister 10. The vacuum can be applied at location 40. The second vacuum line 36 is utilized so as to remove accumulated liquid 38 from the chamber 26. This excess liquid can be removed at location 40, or reintroduced into the vacuum line adjacent outlet 13.

Figure 2:
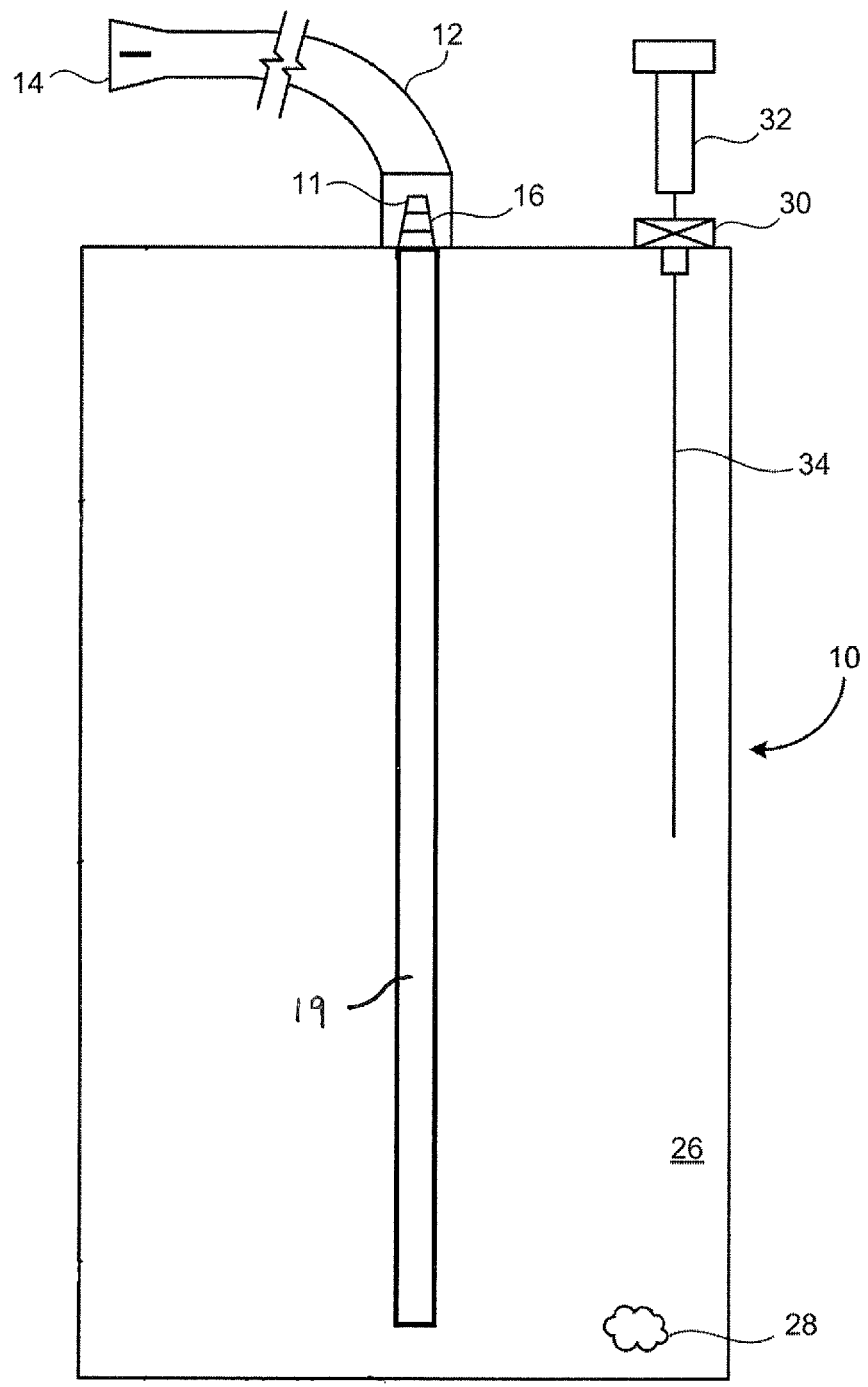

FIG. 2 illustrates a simplified canister 10 for use in the preferred embodiment of the present invention, wherein collected amniotic fluid can be used without additional processing. As shown in FIG. 2, the canister 10 has an internal tube 19 which directs the collected amniotic fluid from the suction line 11 towards the bottom of the chamber 26 of the canister 10. The internal tube 19 is provided in lieu of the coil described above. Heavier cellular material 28 is shown as collecting near the bottom of the chamber due to natural settling. Amniotic fluid collected in the chamber, including heavier cellular material 28, can be collected with the syringe 32 through needle 34 inserted in port 30.

Figure 3:
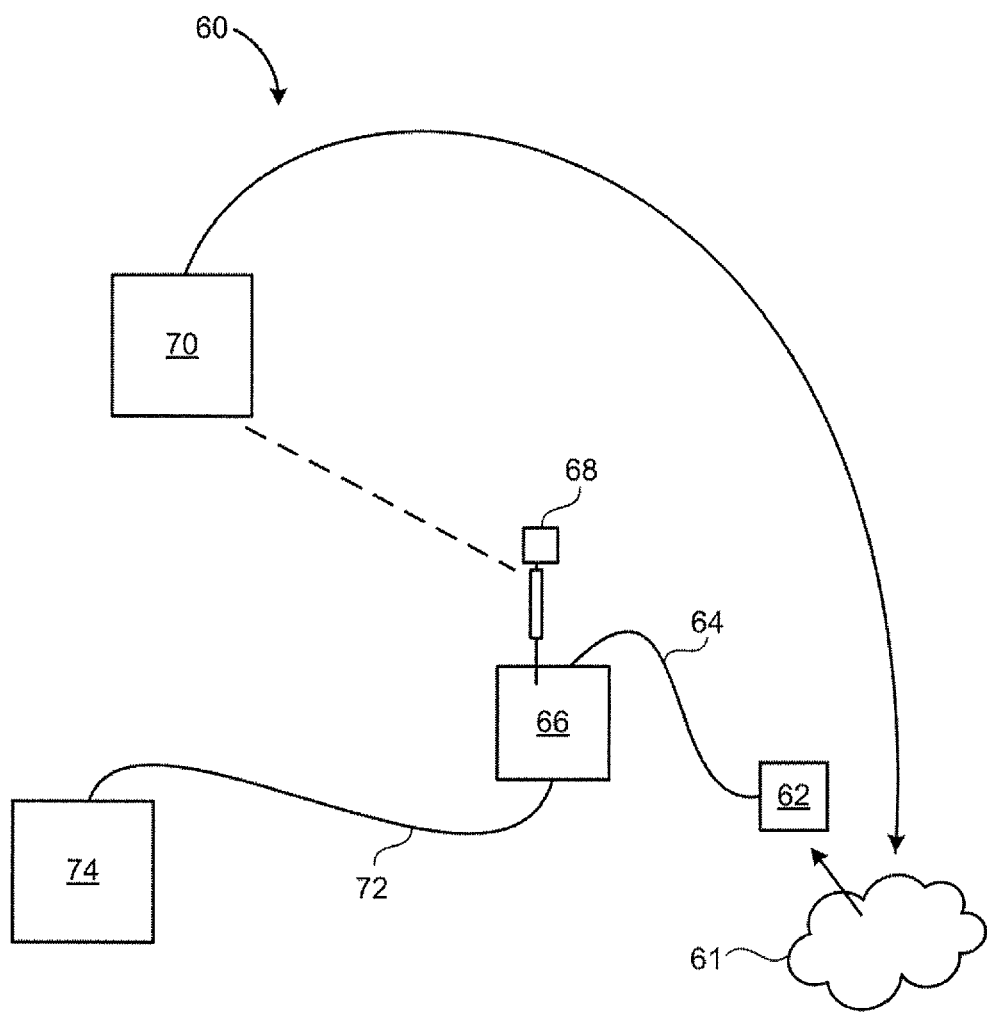
FIG. 3 is a schematic view showing the method of the present invention.

FIG. 3 shows a diagram of the method 60 of the preferred embodiment of the present invention. A collection site 61 is shown in FIG. 3. A suction tip 62 is applied to the collection site 61 so as to collect amniotic fluid. Importantly, the collection of amniotic fluid is accomplished coincident with, rather than before or after, the caesarian section procedure. The amniotic fluid travels through the suction tip 62 and into the line 64. From the line 64, the amniotic fluid enters the canister 66 (as described hereinabove). In an optional step, the separation of the heavier cellular materials, including growth factors, stem cells and platelets, is accomplished in the canister 66. The optional separation is accomplished coincident with the surgical process conducted at the collection site 61.

FIG. 3 also shows how the syringe 68 is inserted into the canister 66. The syringe 68 removes at least some portion of the amniotic fluid from the canister 10 (including any separated heavier cellular material) to a mixing location 70. The location 70 is within the same operating room as the operation is being conducted, and importantly all steps in the method of the present invention are conducted in the single operating room. At location 70, the amniotic fluid is mixed with the coagulant or sealant, and reapplied at the collection site 61, or the location of the wound. Specifically, the mixture is applied at the uterine and facial closure at the surgeon's discretion.

The coagulant or sealant can be calcium chloride, or preferably, hydrogel. When mixed with hydrogel, the amniotic fluid is essentially soaked up by the hyrdogel so as to form a suitable medicine for application to the wound site.

The mixed amniotic fluid and coagulant or sealant has the effect of a natural bandage on the wound site, speeding healing of the wound site. The anti-adhesive and antibacterial effects of the heavier cellular components aid in speeding the healing.

Unlike prior art collection and use of amniotic fluid, the present invention importantly: (1) accomplishes collection, processing and reuse in the same location; (2) reuses the amniotic fluid on the patient from which it was taken (i.e. autologous use); and (3) collects the amniotic fluid during the caesarian section procedure. These differences convey a number of advantages compared to the prior art methods.

Because the mixing of the amniotic fluid occurs coincident with and in the same room as the C-section procedure, this allows for the immediate reuse thereof. As noted hereinabove, if the amniotic fluid were processed in a remote location from the operating room, by the time such processing had occurred, the surgeon would likely have finished the procedure and closed the surgical incision. As such, the amniotic fluid (and beneficial components thereof) cannot be reused on the patient from which they were extracted. Autologous use of the amniotic fluid provides for the a more effective healing outcome, as compared to non-autologous uses of the amniotic fluid. Collection of amniotic fluid during the caesarian section procedure is safer for the patient as compared to collection prior to the caesarian section procedure.

Figure 4:
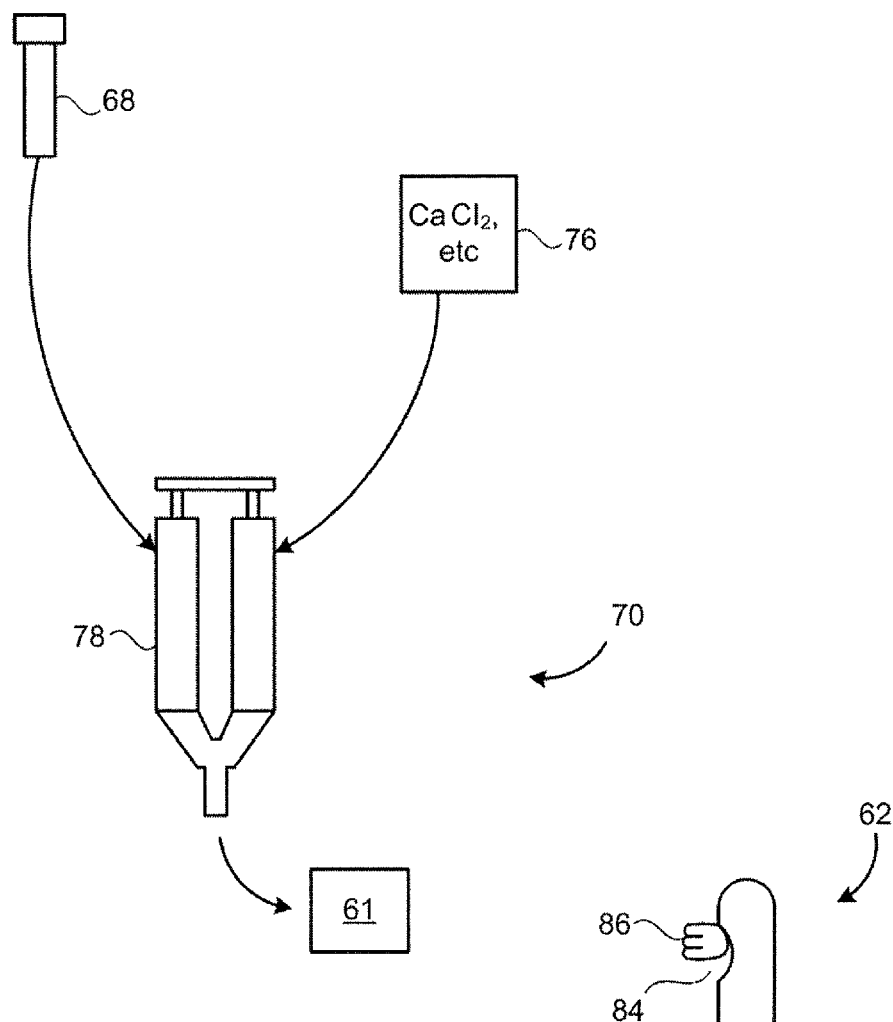
FIG. 4 is a schematic view showing the syringe and dual chambered applicator of the method of the present invention.

Referring to FIG. 4, there is shown how the mixing at location 70 occurs in an embodiment of the invention. The syringe 68 is used to fill one chamber of the dual-chambered applicator 78. The second chamber is filled with a coagulant or sealant 76. The coagulant or sealant 76 can include calcium chloride. The dual-chambered applicator is then used to apply the mixed components path the wound or collection site 61.

Figure 5:
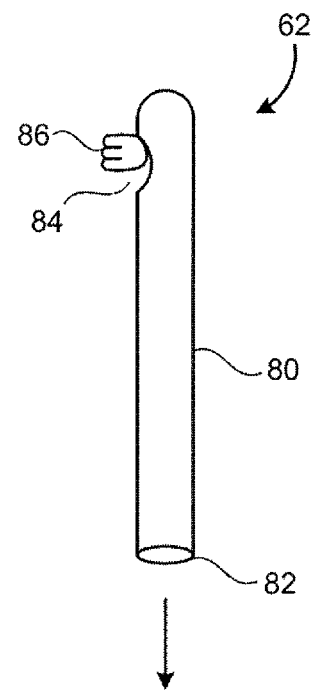
FIG. 5 is a side view showing the Yankauer suction tip of one embodiment of the present invention.

FIG. 5 shows an example of a suction tip 62 in accordance with one embodiment the present invention. The suction tip 62 is a Yankauer suction tip, common in the art, but with the added benefit of a plurality of teeth 86. The suction tip 62 includes a tube 80 which connects at end 82 to the suction line in the operating room. There is an opening 84 through which liquid and other materials can be sectioned. Adjacent this opening 84 are the plurality of scraping teeth 86. A soft tip 88 is also provided. This suction tip 62 of the present invention is particularly suitable for a radial scraping of the placenta at the collection site. This radial scraping would allow for efficient and effective removal of amniotic fluid, as well as the beneficial heavier cellular material from the site.

In one embodiment of the present invention, the system for the collection and separation of the cellular material will be sold as a kit. The kit would necessarily include the novel canister shown in FIG. 2, as well as the syringe and dual chambered applicator with the coagulant or sealant. Optionally, the kit could include the suction tip 62 as shown in FIG. 5, as the suction tip is particularly suitable for the purposes of the kit.

Figure 6:
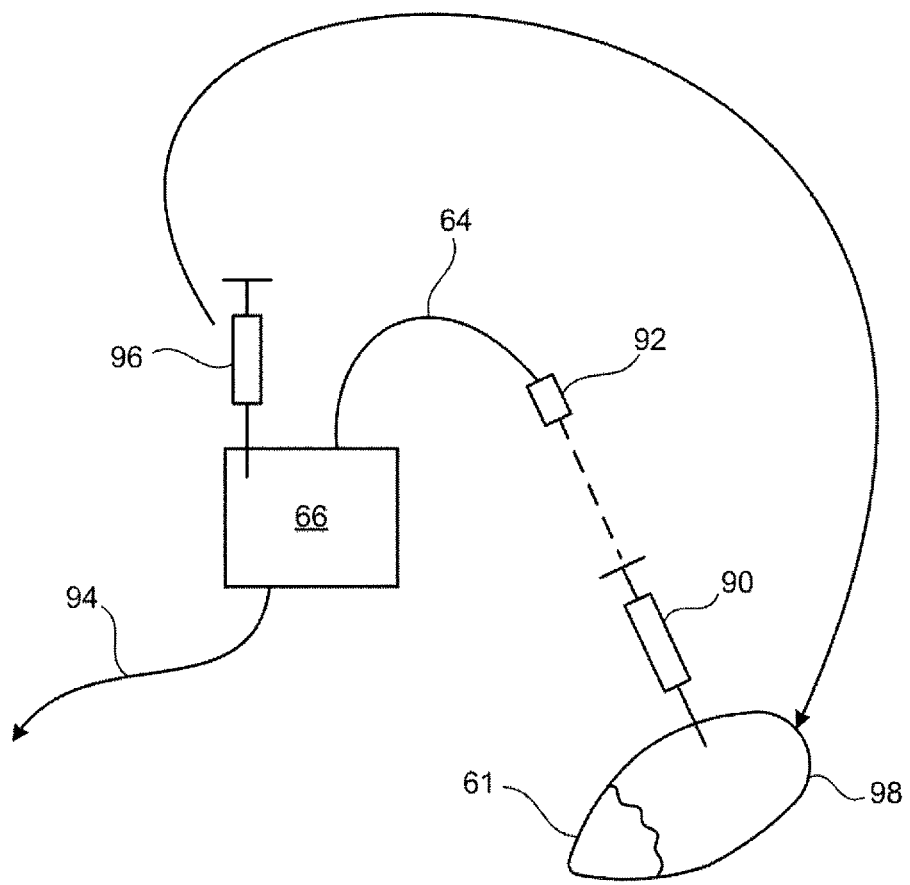
FIG. 6 is a schematic view showing additional steps in the method of the present invention wherein placental aspirate is collected, processed and reused.

The present invention may also include steps to collect, process and reuse placental blood or placental aspirate from the collection site. FIG. 6 shows a schematic view of the placental aspirate collection and processing. Referring to FIG. 6, it can be seen how a second syringe 90 is utilized to draw up placental aspirate from the main vessels and arteries on the fetal placenta side of the placenta. The placenta is shown in FIG. 6 as reference numeral 61. Preferably, the second syringe 90 is a 30 cc syringe. The syringe 90 is then connected to a suction tip 92 so as to draw the collected placental aspirate into the line 64. The line 64, as shown in the previous figures, leads to the canister 66, where the placental aspirate may be processed in the manner that the amniotic fluid was processed as described hereinabove.

Line 94 shows that how the resulting liquid is reused or disposed of. In FIG. 6, it can be seen how a third syringe 96, via a port in the cannister 66, is used to draw up the condensed placental blood, or heavier cellular materials of the placental aspirate therein. Preferably, the third syringe 96 is a 10 cc syringe. The third syringe 96 is then used to spot inject the process condensed placental aspirate along the perimeter 98 of the dermal caesarian section wound before after suturing of the wound Use of the process condensed placental aspirate on the wound further promotes reduced healing time, reduced scarring and increases the antibacterial defense in that area. Collectively, the processing and reuse of the amniotic fluid and placental aspirate should dramatically improve the patient's healing experience.

In a kit in accordance with the embodiment of the present invention wherein placental aspirate is collected, processed and reused, the kit can further include the second and third syringes is 90 and 96, as well as a separate canister 66, if desired. The kit is importantly sterile such that it can be immediately used by the surgeon in the operating room.

Use of the method for the present invention allows for substantially decreased healing time for women undergoing a C-section. Because the processing of the amniotic fluid and placental aspirate occurs coincident with the C-section procedure, there is little extra time necessary in order to provide this natural, healing bandage and injection. As such, surgeons, who are very busy, would likely be willing to use a system and method of the present invention, as a relatively insignificant amount of time is needed to perform it.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A method for collection and use of amniotic fluid comprising the following steps:
    coincident with a caesarian section procedure, suctioning amniotic fluid from a caesarian section collection site using a vacuum line;
    passing the suctioned amniotic fluid into a canister positioned along or in communication with the vacuum line;
    removing at least some of the passed amniotic fluid from the canister;
    mixing the removed amniotic fluid with either of a coagulant or a sealant; and
    applying the mixed amniotic fluid to the caesarian section collection site using an applicator, wherein each of the steps are conducted in a single operating room.

2. The method of claim 1, said step of removing comprising:
    providing a port on said canister;
    inserting a syringe needle into said port; and
    drawing amniotic fluid into an interior of said syringe needle.

3. The method of claim 1, said coagulant or sealant comprising calcium chloride.

4. The method of claim 1, said coagulant or sealant comprising hydrogel.

5. The method of claim 1, further comprising the following steps:
    collecting placental aspirate;
    passing the collected placental aspirate into a second canister;
    removing at least some of the passed placental aspirate from the canister;
    mixing the removed placental aspirate with either of a coagulant or a sealant; and
    injecting the mixed placental aspirate into said caesarian section collection site.

6. The method of claim 1, said at least some of the passed amniotic fluid comprising heavier cellular material, the method comprising the additional step of:
    separating heavier cellular material from the passed amniotic fluid inside said canister.

* * * * *